United States Patent
Benicewicz et al.

(10) Patent No.: US 6,458,968 B2
(45) Date of Patent: Oct. 1, 2002

(54) DITHIOCARBOXYLIC ESTER SYNTHETIC PROCESS

(75) Inventors: Brian C. Benicewicz, Loudonville, NY (US); Subbareddiar Kanagasabapathy, Shrewsbury, MA (US); Arumugam Sudalai, Troy, NY (US)

(73) Assignee: Rensselaer Polytechnic Institute, Troy, NY (US)

( * ) Notice: Subject to any disclaimer, the term of this patent is extended or adjusted under 35 U.S.C. 154(b) by 0 days.

(21) Appl. No.: 09/877,455

(22) Filed: Jun. 8, 2001

Related U.S. Application Data

(60) Provisional application No. 60/210,517, filed on Jun. 9, 2000.

(51) Int. Cl.[7] .................... C07D 333/22; C07D 333/16; C07C 69/63
(52) U.S. Cl. ............................ 549/70; 549/78; 560/230
(58) Field of Search ....................... 549/70, 78; 560/230

(56) References Cited

FOREIGN PATENT DOCUMENTS

WO       WO 98/01478       1/1998

OTHER PUBLICATIONS

Stenzel–Rosenbaum et al, "Star–polymer synthesis via radical reversible addition–fragmentation chain–transfer polymerization" CA135:273326, 2001.*
Zhuang, Rongchuan et al, "Synthesis of A–B type block coploymers using 1–phenylethyl dithiobenzoate as RAFT agent", CA135:181016, 2001.*
Le, Tam Phuong et al, "Polymerization with living characteristics with controlled dispersity. . .", CA128:115390.*

* cited by examiner

Primary Examiner—Deborah C. Lambkin

(74) Attorney, Agent, or Firm—Heslin Rothenberg Farley & Mesiti P.C.; Mary Louise Gioeni

(57) ABSTRACT

A process the preparation of a dithiocarboxylic esters comprises reacting a carboxylic acid compound of formula $R^1(COOH)_m$, a compound of formula $R^2AH$ and phosphorus pentasulfide to produce a compound of structure I. An alternate process comprises reacting a

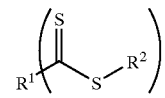

I compound of formula $R^3(COAH)_m$ and a compound of structure II

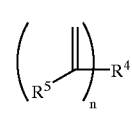

II in the presence of a clay catalyst; and treating products of the reaction with a thiating agent to produce a compound of structure III, a compound of structure IV, or a combination of compounds of structure III and structure IV.

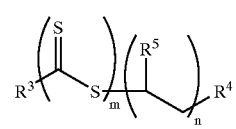

III

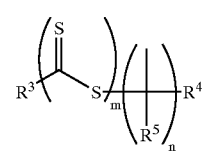

IV

25 Claims, No Drawings

DITHIOCARBOXYLIC ESTER SYNTHETIC PROCESS

CROSS REFERENCE TO RELATED APPLICATIONS

This application claims priority from U.S. Provisional Application Ser. No. 60/210,517, filed on Jun. 9, 2000.

FIELD OF THE INVENTION

The invention relates to dithiocarboxylic esters and processes for the preparation thereof.

BACKGROUND OF THE INVENTION

Living polymerization is a method by which polymers having a narrow molecular weight distribution may be obtained. Block copolymers may also be synthesized using the method. Block copolymers may display improved mechanical and/or chemical properties over corresponding random copolymers. Commercial processes for the production of block copolymers typically employ anionic initiators in living polymerization processes. Polymerization processes using free radical initiators have many attractive characteristics and have attained commercial importance. However, these do not include processes with characteristics of living polymerization.

One promising method for free radical polymerization with living characteristics is reversible addition-fragmentation chain transfer (RAFT) polymerization (Moad, 1998). Use of thiocarbonylthio (dithiocarboxylic ester) compounds of structure

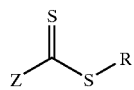

chain transfer agents for RAFT polymerizations is described in International Application Number PCT/US97/12540, published as WO 98/01478 on Jan. 15, 1998. Free radical processes employing these chain transfer agents resulted in polymers having low polydispersity in bulk, emulsion and solution polymerizations. Block copolymers were also successfully prepared.

However, known methods for synthesis of the chain transfer agents are unsatisfactory for various reasons. Literature methods for preparation of dithiocarboxylic esters include: alkylation of $ArCS_2M$ (M=Na or K) or $ArCS_2MgX$ with an appropriate alkyl or aryl halide, thiation of S-substituted thioesters using Lawesson's reagent, transesterifications of dithioesters with thiols, and reaction of bis(thiocarbonyl)disulfides with azo compounds. Disadvantages of these methods include safety, cost and sensitivity concerns regarding the use of Grignard reagents, inability to utilize desirable probe functionalities because of incompatibility with reagents, lack of suitable thiol, thioacid and/or disulfide precursors and, ultimately, low yield from the reactions. It is therefore an object of the present invention to provide a process for the synthesis of dithiocarboxylic esters that eliminates the use of Grignard reagents, allows for synthesis of functional dithiocarboxylic esters, requires inexpensive and readily available starting materials, and provides high yields.

SUMMARY OF THE INVENTION

It has been unexpectedly discovered that the processes of the present invention provide an improved method for the synthesis of dithiocarboxylic esters which meets these requirements. In addition, the process operates under mild conditions, and provides for facile isolation of products.

In one aspect, a process according to the present invention for the preparation of a dithiocarboxylic ester of structure I

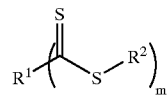

comprises reacting a carboxylic acid compound of formula $R^1(COOH)_m$, a compound of formula $R^2AH$ and phosphorus pentasulfide, wherein $R^1$ is a m-valent radical selected from the group consisting of alkyl, substituted alkyl, aryl, substituted aryl, heteroaryl, substituted heteroaryl; $R^2$ is selected from the group consisting of alkyl, substituted alkyl, aryl, substituted aryl, heteroaryl, substituted heteroaryl, alkylaryl, and substituted alkylaryl; A is S or O; and m is an integer from 1–6.

In another aspect, a process according to the present invention comprises:

(a) reacting a compound of formula $R^3(COAH)_m$ and a compound of structure II

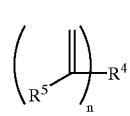

in the presence of a clay catalyst; and (b) treating products of the reaction with a thiating agent to produce a compound of structure III, a compound of structure IV, or a combination of compounds of structure III and structure IV;

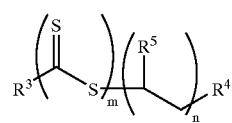

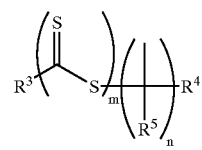

wherein $R^3$ is selected from the group consisting of alkyl, substituted alkyl, aryl, substituted aryl, heteroaryl, substituted heteroaryl; $R^4$ is a n-valent radical selected from the group consisting of alkyl, substituted alkyl, aryl, substituted aryl, heteroaryl, substituted heteroaryl; $R^5$ is H or lower alkyl; and A is S or O.

Definitions

In the context of the present invention, alkyl is intended to include linear, branched, or cyclic hydrocarbon structures and combinations thereof. Lower alkyl refers to alkyl groups of from 1 to 4 carbon atoms. Examples of lower alkyl groups include methyl, ethyl, propyl, isopropyl, butyl, s- and t-butyl. Preferred alkyl groups are those of $C_{20}$ or below. Cycloalkyl is a subset of alkyl and includes cyclic hydrocarbon groups of from 3 to 8 carbon atoms. Examples of cycloalkyl groups include c-propyl, c-butyl, c-pentyl, and norbornyl Alkoxy or alkoxyl refers to groups of from 1 to 8 carbon atoms of a straight, branched, cyclic configuration and combinations thereof attached to the parent structure through an oxygen. Examples include methoxy, ethoxy, propoxy, isopropoxy, cyclopropyloxy, and cyclohexyloxy. Lower alkoxy refers to groups containing one to four carbons.

Acyl refers to groups of from 1 to 8 carbon atoms of a straight, branched, cyclic configuration, saturated, unsaturated and aromatic and combinations thereof, attached to the parent structure through a carbonyl functionality. One or more carbons in the acyl residue may be replaced by nitrogen, oxygen or sulfur as long as the point of attachment to the parent remains at the carbonyl. Examples include acetyl, benzoyl, propionyl, isobutyryl, t-butoxycarbonyl, and benzyloxycarbonyl. Lower-acyl refers to groups containing one to four carbons.

Aryl and heteroaryl mean a 5- or 6-membered aromatic or heteroaromatic ring containing 0–3 heteroatoms selected from nitrogen, oxygen or sulfur; a bicyclic 9- or 10-membered aromatic or heteroaromatic ring system containing 0–3 heteroatoms selected from Nitrogen, oxygen or sulfur; or a tricyclic 13- or 14-membered aromatic or heteroaromatic ring system containing 0–3 heteroatoms selected from Nitrogen, oxygen or sulfur. Each of these rings is optionally substituted with 1–3 lower alkyl, substituted alkyl, substituted alkynyl, carbonyl, nitro, halogen, haloalkyl, hydroxy, alkoxy, $OCH(COOH)_2$, cyano, primary amino, secondary amino, acylamino, phenyl, benzyl, phenoxy, benzyloxy, heteroaryl, or heteroaryloxy; each of said phenyl, benzyl, phenoxy, benzyloxy, heteroaryl, and heteroaryloxy is optionally substituted with 1–3 substitutents selected from lower alkyl, alkenyl, alkynyl, halogen, hydroxy, haloalkyl, alkoxy, cyano, phenyl, benzyl, benzyloxy, carboxamido, heteroaryl, heteroaryloxy, nitro or —NRR (wherein R is independently H, lower alkyl or cycloalkyl, and —RR may be fused to form a cyclic ring with nitrogen). The aromatic 6- to 14-membered carbocyclic rings include, for example, benzene, naphthalene, indane, tetralin, and fluorene; and the 5- to 10-membered aromatic heterocyclic rings include, e.g., imidazole, pyridine, indole, thiophene, benzopyranone, thiazole, furan, benzimidazole, quinoline, isoquinoline, quinoxaline, pyrimidine, pyrazine, tetrazole and pyrazole.

Alkylaryl means an alkyl residue attached to an aryl ring. Examples are benzyl and phenethyl. Heteroarylalkyl means an alkyl residue attached to a heteroaryl ring. Examples include pyridinylmethyl and pyrimidinylethyl.

Heterocycle means a cycloalkyl or aryl residue in which one to two of the carbons is replaced by a heteroatom such as oxygen, nitrogen or sulfur. Examples of heterocycles that fall within the scope of the invention include pyrrolidine, pyrazole, pyrrole, indole, quinoline, isoquinoline, tetrahydroisoquinoline, benzofuran, benzodioxan, benzodioxole (commonly referred to as methylenedioxyphenyl, when occurring as a substituent), tetrazole, morpholine, thiazole, pyridine, pyridazine, pyrimidine, thiophene, furan, oxazole, oxazoline, isoxazole, dioxane, and tetrahydrofuran.

Substituted alkyl, aryl, cycloalkyl, or heterocyclyl refer to alkyl, aryl, cycloalkyl, or heterocyclyl wherein up to three H atoms in each residue are replaced with halogen, haloalkyl, hydroxy, lower alkoxy, carboxy, carboalkoxy, carboxamido, cyano, carbonyl, nitro, primary amino, secondary amino, alkylthio, sulfoxide, sulfone, acylamino, amidino, phenyl, benzyl, heteroaryl, phenoxy, benzyloxy, heteroaryloxy, or substituted phenyl, benzyl, heteroaryl, phenoxy, benzyloxy, or heteroaryloxy.

In yet another aspect, the present invention relates to dithiocarboxylic esters having the following structures:

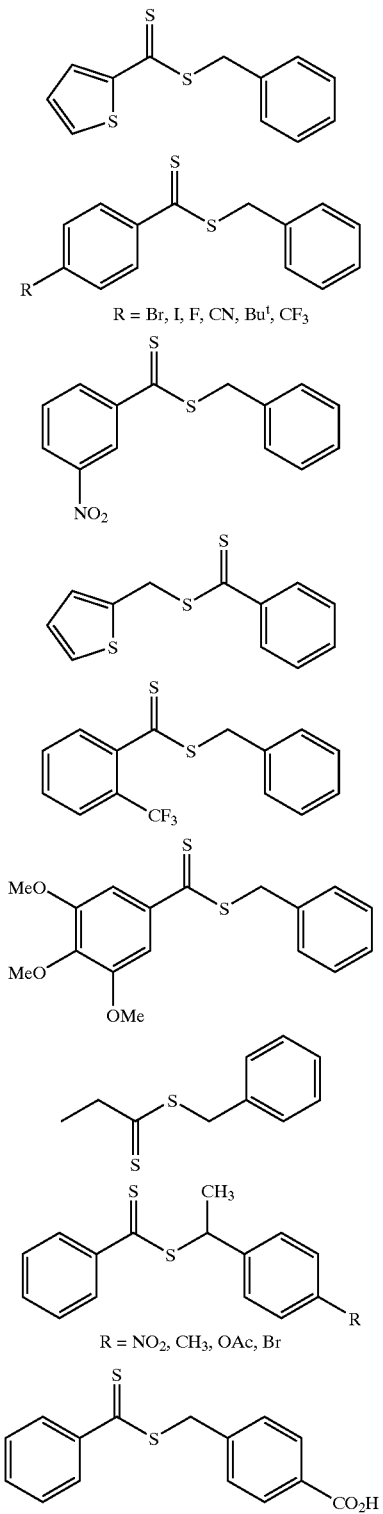

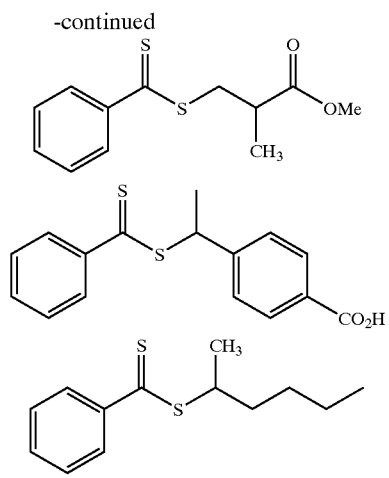

DETAILED DESCRIPTION OF THE INVENTION

The present invention is more easily understood when reference is made to general Schemes A and B for the preparation of dithiocarboxylic esters.

Scheme A

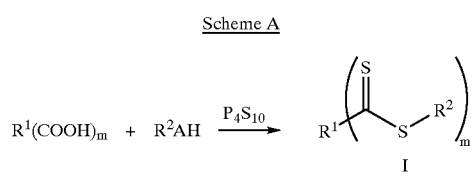

Scheme B

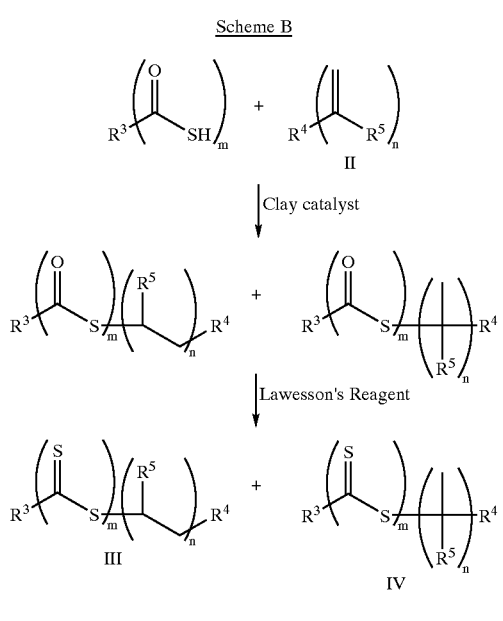

In one embodiment, a process according to the present invention comprises reacting a carboxylic acid compound of formula $R^1(COOH)_m$, a compound of formula $R^2AH$ and phosphorus pentasulfide, to form a dithiocarboxylic ester of structure I,

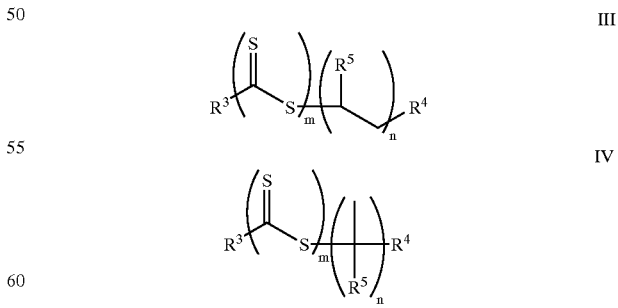

where $R^1$ represents a m-valent radical selected from the group consisting of alkyl, substituted alkyl, aryl, substituted aryl, heteroaryl, substituted heteroaryl; $R^2$ represents alkyl, substituted alkyl, aryl, substituted aryl, heteroaryl, substituted heteroaryl, alkylaryl, and substituted alkylaryl; A represents S or O; and m is an integer from 1–6. This process is illustrated in Scheme A. In the scheme, one equivalent of a carboxylic acid compound reacts with one equivalent of an alcohol or thiol in the presence of one equivalent of phosphorus pentasulfide. Preferred dithiocarboxylic esters that may be prepared by the process are benzyl dithiobenzoate, benzyl-4-methoxydithiobenzoate, benzyl-4-fluorodithiobenzoate, benzyl-4-nitrodithiobenzoate, benzyl-4-cyanodithiobenzoate, benzyl-4-trifluoromethyldithiobenzoate, diphenyldithiobenzoate, propyl dithiobenzoate, benzyl dithiopropionate, and benzyl-4-chlorodithiobenzoate.

Phosphorus pentasulfide is known as a thiating agent for amides, ketones, aldehydes, esters, and thioesters. Typically, a 1:1:1 proportion of acid to alcohol/thiol to phosphorus pentasulfide is used. In some cases, it may be necessary to use an excess of the reagent to convert the esters to dithioesters. It will be noted that where substitutents of the substituted alkyl, aryl, alkylaryl or heteroaryl groups are amides, ketones, aldehydes, or esters, these groups may or may not be converted by the thiating agent to the corresponding S-containing compound. If an undesired conversion is expected to occur, it may be avoided by protecting the groups with a suitable protecting agent.

In another embodiment, a process according to the present invention comprises reacting a compound of formula $R^3(COAH)_m$, and a compound having structure II

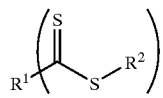
II in the presence of a clay catalyst; and treating products of the reaction with a thiating agent to produce a dithiocarboxylic ester of structure III, a compound of structure IV, or a combination of compounds of structure III and structure IV.

III

IV $R^3$ may be alkyl, substituted alkyl, aryl, substituted aryl, heteroaryl, substituted heteroaryl; $R^4$ is a n-valent radical selected from the group consisting of alkyl, substituted alkyl, aryl, substituted aryl, heteroaryl, substituted heteroaryl; $R^5$ is H or lower alkyl; A is S or O; and m and n are independently integers from 1–6, with the proviso that when m>1, n=1 and when n>1, m=1. Preferred dithiocarboxylic esters 1–10 that may be prepared by the process are shown in Table 1.

TABLE 1

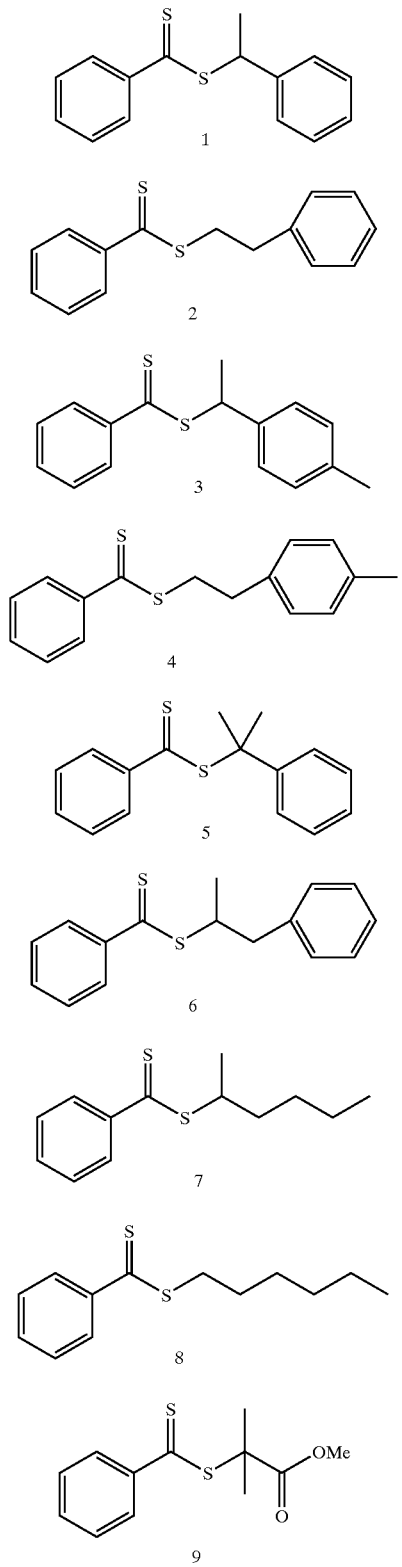

TABLE 1-continued

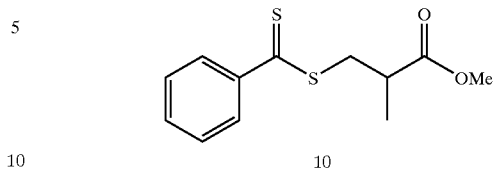

10

Thiating agents include phosphorus pentasulfide or Lawesson's reagent, 2,4-bis-(4-methoxyphenyl)-1,3,2,4-dithiadiphosphetane 2,4-disulfide. Preferably, the thiating agent is Lawesson's reagent.

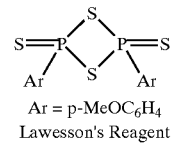

Ar = p-MeOC$_6$H$_4$
Lawesson's Reagent

As noted above, substituent groups, including amides, ketones, aldehydes, or esters, may or may not be converted by the thiating agent to the corresponding S-containing compound. For example, in a reaction between thiobenzoic acid and methylmethacrylate (MMA) according to Scheme B, the thioester group was converted to a dithioester, while the ester derived from MMA remained unconverted. If desired, the convertible group may be masked with a protecting group.

Suitable compounds of structure II include vinyl compounds, olefins, acrylates and methacrylates and styrene and styrene derivatives. Preferred compounds of this type are vinyl acetate, acrylate and methacrylate esters, styrene, α-methylstyrene and p-methylstyrene. Divalent compounds, such as divinylbenzene, may also be used.

Suitable solvents for the reactions of Schemes A and B typically include ethers, aromatics, tertiary amines and chlorinated solvents pyridine, DMF, dioxane, acetonitrile, and THF. Toluene and benzene are preferred solvents. As phosphorus pentasulfide reacts with DMSO, primary and secondary amines, alcohols and neutral or acidic water, these solvents are generally avoided.

The reactions in Scheme A and B proceed under a wide range of temperature conditions, and preferably, from about 0° C. to about 150° C. More preferably, the temperature ranges from about 80° C. to about 110° C.

In order to fully illustrate the nature of the present invention and the manner of practicing the same, the following examples are presented:

EXAMPLES

Example 1

Preparation of benzyl dithiobenzoate

A mixture of benzoic acid (1.22 g), benzyl mercaptan (1.24 g) and phosphorus pentasulfide (4.44 g) in toluene (40 ml) was refluxed for 10 h. A dark red color was developed immediately after heating. After the reaction was complete (as monitored by GC-MS), it was cooled to room temperature and purified by column chromatography packed with-.neutral alumina, eluting with benzene. Removal of the solvent by distillation gave the single compound, benzyl dithiobenzoate (2.22 g, 91%). It was further characterized by $^1$H and $^{13}$C-NMR.

Example 2

Preparation of benzyl-4-methoxydithiobenzoate

A mixture of 4-methoxybenzoic acid (1.52 g), benzyl mercaptan (1.24 g) and phosphorus pentasulfide (4.44 g) in toluene (40 ml) was refluxed for 12 h. A dark red color was developed immediately after heating. After the reaction was complete (as monitored by GC-MS), it was cooled to room temperature and purified by a column chromatography packed with neutral alumina, eluting with benzene. Removal of the solvent by distillation gave the single compound, benzyl-4-methoxydithiobenzoate (1.89 g, 69%). It was further characterized by $^1$H and $^{13}$C-NMR.

Example 3

Preparation of benzyl-4-fluorodithiobenzoate

A mixture of 4-fluorobenzoic acid (1.40 g), benzyl mercaptan (1.24 g) and phosphorus pentasulfide (4.44 g) in toluene (40 ml) was refluxed for 12 h. A dark red color was developed immediately after heating. After the reaction was complete (as monitored by GC-MS), it was cooled to room temperature and purified by a column chromatography packed with neutral alumina, eluting with benzene. Removal of the solvent by distillation gave the single compound, benzyl-4-fluorodithiobenzoate (1.86 g, 71%). It was further characterized by $^1$H and $^{13}$C-NMR.

Example 4

Preparation of benzyl-4-nitrodithiobenzoate

A mixture of 4-nitrobenzoic acid (1.67 g), benzyl mercaptan (1.24 g) and phosphorus pentasulfide (4.44 g) in toluene (40 ml) was refluxed for 20 h. A dark red color was developed immediately after heating. After the reaction was complete (as monitored by GC-MS), it was cooled to room temperature and purified by a column chromatography packed with neutral alumina, eluting with benzene. Removal of the solvent by distillation gave the single compound, benzyl-4-nitrodithiobenzoate (1.48 g, 51%). It was further characterized by $^1$H and $^{13}$C-NMR.

Example 5

Preparation of benzyl-4-cyanodithiobenzoate

A mixture of 4 cyanobenzoic acid (1.47 g), benzyl mercaptan (1.24 g) and phosphorus pentasulfide (4.44 g) in toluene (40 ml) was refluxed for 20 h. A dark red color was developed immediately after heating. After the reaction was complete (as monitored by GC-MS), it was cooled to room temperature and purified by a column chromatography packed with neutral alumina, eluting with benzene. Removal of the solvent by distillation gave the single compound, benzyl-4-cyanodithiobenzoate (1.15 g, 43%). It was further characterized by $^1$H and $^{13}$C-NMR.

Example 6

Preparation of benzyl-4-trifluoromethyldithiobenzoate

A mixture of 4-trifluoromethylbenzoic acid (1.90 g), benzyl mercaptan (1.24 g) and phosphorus pentasulfide (4.44 g) in toluene (40 ml) was refluxed for 10 h. A dark red color was developed immediately after heating. After the reaction was complete (as monitored by GC-MS), it was cooled to room temperature and purified by a column chromatography packed with neutral alumina, eluting with benzene. Removal of the solvent by distillation gave the single compound, benzyl-4-trifluoromethyidithiobenzoate (2.30 g, 74%). It was further characterized by $^1$H and $^{13}$C-NMR.

Example 7

Preparation of diphenyldithiobenzoate

A mixture of benzoic acid (1.22 g), thiophenol (1.10 g) and phosphorus pentasulfide (4.44 g) in toluene (40 ml) was refluxed for 8 h. A dark red color was developed immediately after heating. After the reaction was complete (as monitored by GC-MS), it was cooled to room temperature and purified by a column chromatography packed with neutral alumina, eluting with benzene. Removal of the solvent by distillation gave the single compound, diphenyl dithiobenzoate (1.56 g, 68%). It was further characterized by $^1$H and $^{13}$C-NMR.

Example 8

Preparation of propyl dithiobenzoate

A mixture of benzoic acid (1.22 g), 1-propanethiol (0.76 g) and phosphorus pentasulfide (4.44 g) in toluene (40 ml) was refluxed for 10 h. A dark red color was developed immediately after heating. After the reaction was complete (as monitored by GC-MS), it was cooled to room temperature and purified by a column chromatography packed with neutral alumina, eluting with benzene. Removal of the solvent by distillation gave the single compound, propyl dithiobenzoate (1.21 g, 62%). It was further characterized by $^1$H and $^{13}$C-NMR.

Example 9

Preparation of benzyl dithiopropionate

A mixture of propionic acid (0.74 g), benzyl mercaptan (1.24 g) and phosphorus pentasulfide (4.44 g) in toluene (40 ml) was refluxed for 10 h. A dark red color was developed immediately after heating. After the reaction was complete (as monitored by GC-MS), it was cooled to room temperature and purified by a column chromatography packed with neutral alumina, eluting with benzene. Removal of the solvent by distillation gave the desired compound, benzyl dithiopropionate (0.98 g, 50%) without further purification. The structure was confirmed by $^1$H and $^{13}$C-NMR.

Example 10

Preparation of benzyl dithiobenzoate

A mixture of benzoic acid (1.22 g), benzyl alcohol (1.08 g) and phosphorus pentasulfide (4.44 g) in benzene (40 ml) was refluxed for 10 h. A dark red color was developed immediately after heating. After the reaction was complete (as monitored by GC-MS), it was cooled to room temperature and purified by a column chromatography packed with neutral alumina, eluting with benzene. Removal of the solvent by distillation gave the desired compound, benzyl dithiobenzoate (1.70 g, 70%) without further purification. The structure was confirmed by $^1$H and $^{13}$C-NMR.

Example 12

Preparation of benzyl-4-methoxydithiobenzoate

A mixture of 4-methoxybenzoic acid (1.52 g), benzyl alcohol (1.08 g) and phosphorus pentasulfide (4.44 g) in benzene(40 ml) was refluxed for 12 h. A dark red color was developed immediately after heating. After the reaction was complete (as monitored by GC-MS), it was cooled to room temperature and purified by a column chromatography packed with neutral alumina, eluting with benzene. Removal of the solvent by distillation gave the required compound, benzyl-4-methoxydithiobenzoate (1.69 g, 62%) as the major product. The structure was confirmed by $^1$H- and $^{13}$C-NMR.

Example 13

Preparation of benzyl-4-fluorodithiobenzoate

A mixture of 4-fluorobenzoic acid (1.40 g), benzyl alcohol (1.08 g) and phosphorus pentasulfide (4.44 g) in benzene (40 ml) was refluxed for 12 h. A dark red color was developed immediately after heating. After the reaction was complete (as monitored by GC-MS), it was cooled to room temperature and purified by a column chromatography packed with neutral alumina, eluting with benzene. Removal of the solvent by distillation gave the required compound, benzyl-4-fluorodithiobenzoate (1.36 g, 52%) without further purification. The structure was confirmed by $^1$H and $^{13}$C-NMR.

Example 14

Preparation of benzyl-4-chlorodithiobenzoate

A mixture of 4-nitrobenzoic acid (1.67 g), benzyl alcohol (1.08 g) and phosphorus pentasulfide (4.44 g) in benzene (40 ml) was refluxed for 20 h. A dark red color was developed immediately after heating. After the reaction was complete (as monitored by GC-MS), it was cooled to room temperature and purified by a column chromatography packed with neutral alumina, eluting with benzene. Removal of the solvent by distillation gave the desired compound, benzyl-4-chlorodithiobenzoate (1.83 g, 66%) without further purification. The structure was confirmed by 1H and $^{13}$C-NMR.

Example 15

A 50-ml round bottomed flask under nitrogen atmosphere was charged with 20 g of benzene, 100 mg of Montmorillonite (K-10) clay as catalyst 0.75 g of freshly distilled styrene and 1 g of thiobenzoic acid. The whole mixture was degassed with nitrogen for 15 minutes. The heterogeneous mixture was heated to reflux over the course of 10 minutes. The thiobenzoic acid conversion was determined at various times by GC-MS. The unreacted thiobenzoic acid was washed off completely using aqueous base (NaHCO3). The resulting product was analyzed by GC-MS, 1H and 13C NMR. The conversion of thiobenzoic acid after 1440 minutes was 70% and the selectivity for the product 1 and 2 was 75% and 5% respectively.

1

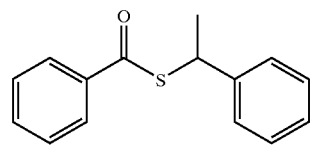

-continued

2

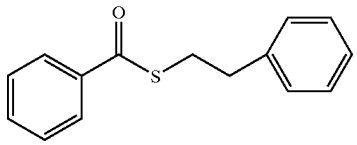

Example 16

A 50-ml round bottomed flask under nitrogen atmosphere was charged with 20 g of benzene, 100 mg of Montmorillonite (KSF) clay as catalyst, 0.75 g of freshly distilled styrene and 1 g of thiobenzoic acid. The whole mixture was degassed with nitrogen for 15 minutes. The heterogeneous mixture was heated to reflux over the course of 10 minutes. The thiobenzoic acid conversion was determined by GC-MS. The unreacted thiobenzoic acid was washed off completely using aqueous base (NaHCO3). The resulting product was analyzed by GC-MS, 1H and 13C NMR. The conversion of thiobenzoic acid after 1440 minutes was 78% and the selectivity for the product 1 and 2 was 49% and 29% respectively.

Example 17

A 50-ml round bottomed flask under nitrogen atmosphere was charged with 20 g of benzene, 100 mg of Montmorillonite (K-10) clay as catalyst, 0.75 g of styrene and 1 g of thiobenzoic acid. The whole mixture was degassed with nitrogen for 15 minutes. The heterogeneous mixture was stirred at room temperature for 960 minutes. The thiobenzoic acid conversion was determined by GC-MS. The unreacted thiobenzoic acid was washed off completely using aqueous base (NaHCO3). The resulting product was analyzed by GC-MS, 1H and 13C NMR. The conversion of thiobenzoic acid after 960 minutes was 94% and the selectivity for the product 1 and 2 was 6% and 76% respectively.

Example 18

A 50-ml round bottomed flask under nitrogen atmosphere was charged with 20 g of benzene, 100 mg of Montmorillonite (K-10) clay as catalyst, 0.86 g of p-methylstyrene and 1 g of thiobenzoic acid. The whole mixture was degassed with nitrogen for 15 minutes. The heterogeneous mixture was heated to reflux over the course of 10 minutes. The thiobenzoic acid conversion was determined by GC-MS. The unreacted thiobenzoic acid was washed off completely using aqueous base (NaHCO3). The resulting product was analyzed by GC-MS, 1H and 13C NMR. The conversion of thiobenzoic acid after 960 minutes was 76% and the selectivity for the product 3 and 4 was 41% and 25% respectively.

3

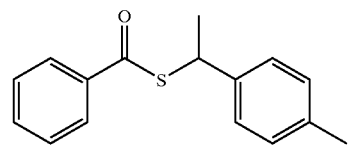

-continued

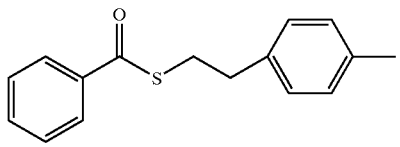

4

Example 19

A 50-ml round bottomed flask under nitrogen atmosphere was charged with 20 g of benzene, 100 mg of Montmorillonite (K-10) clay as catalyst, 0.86 g of α-methylstyrene and 1 g of thiobenzoic acid. The mixture was degassed with nitrogen for 15 minutes. The heterogeneous mixture was heated to reflux over the course of 10 minutes. The thiobenzoic acid conversion was determined by GC-MS. The unreacted thiobenzoic acid was washed off completely using aqueous base (NaHCO3). The resulting product was analyzed by GC-MS, 1H and 13C NMR. The conversion of thiobenzoic acid after 960 minutes was 80% and the selectivity for the product 5 and 6 was 76% and 3% respectively.

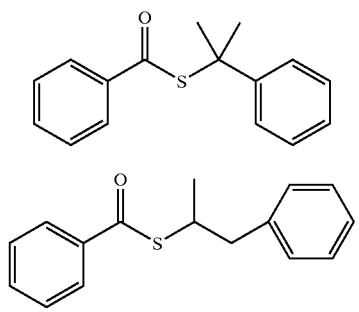

5

6

Example 20

A 50-ml round bottomed flask under nitrogen atmosphere was charged with 20 g of benzene, 100 mg of Montmorillonite (K-10) clay as catalyst, 0.58 g of 1-hexene and 1 g of thiobenzoic acid. The whole mixture was degassed with nitrogen for 15 minutes. The heterogeneous mixture was heated to reflux over the course of 10 minutes. The thiobenzoic acid conversion was determined by GC-MS. The unreacted thiobenzoic acid was washed off completely using aqueous base (NaHCO3). The resulting product was analyzed by GC-MS, 1H and 13C NMR. The conversion of thiobenzoic acid after 960 minutes was 85% and the selectivity for products 7 and 8 was 65% and 20% respectively.

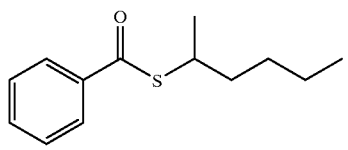

7

-continued

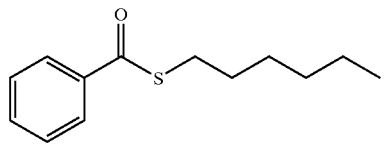

8

Example 21

A 50-ml round bottomed flask under nitrogen atmosphere was charged with 20 g of benzene, 100 mg of Montmorillonite (K-10) clay as catalyst, 0.72 g of MMA and 1 g of thiobenzoic acid. The whole mixture was degassed with nitrogen for 15 minutes. The heterogeneous mixture was heated to reflux over the course of 10 minutes. The thiobenzoic acid conversion was determined by GC-MS. The unreacted thiobenzoic acid was washed off completely using aqueous base (NaHCO3). The resulting product was analyzed by GC-MS, 1H and 13C NMR. The conversion of thiobenzoic acid after 960 minutes was 96% and the selectivity for products 9 and 10 was 58% and 14% respectively.

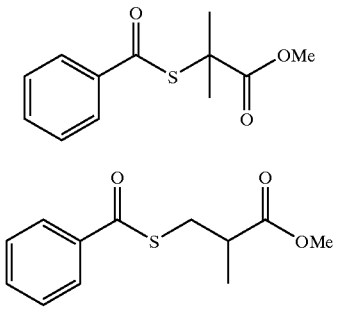

9

10

Example 22

A 25-ml round bottomed flask under nitrogen atmosphere was charged with 10 g of toluene, 500 mg Lawesson's reagent and 450 mg of structure I. The whole mixture was degassed with nitrogen for 15 minutes. The mixture was heated to reflux over the course of 10 minutes and continued for 2 hrs. The crude product was purified by passing through neutral alumna. The resulting product was analyzed by GC-MS, 1H and 13C NMR. The yield of dithicarboxylic acid of structure II was 95%.

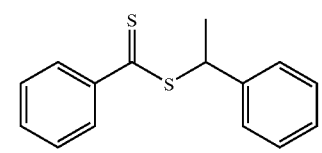

11

What is claimed is:
1. A process for the preparation of a dithiocarboxylic ester of structure I,

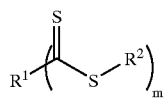

said process comprising reacting a carboxylic acid compound of formula $R^1(COOH)_m$, a compound of formula $R^2AH$ and phosphorus pentasulfide, wherein $R^1$ is a m-valent radical selected from the group consisting of alkyl, substituted alkyl, aryl, substituted aryl, heteroaryl, substituted heteroaryl;

$R^2$ is selected from the group consisting of alkyl, substituted alkyl, aryl, substituted aryl, heteroaryl, substituted heteroaryl, alkylaryl, and substituted alkylaryl;

A is S or O; and m is an integer from 1–6.

2. A process according to claim 1 wherein substitutents of said substituted alkyl, substituted aryl, substituted alkylaryl and substituted heteroaryl are independently chosen from alkyl, halogen, lower alkoxy, cyano, hydroxy and haloalkyl.

3. A process according to claim 1 wherein $R^1$ is selected from the group consisting of alkyl, aryl, and substituted aryl; and $R^2$ is selected from the group consisting of alkyl, aryl, and heteroaryl.

4. A process according to claim 1 wherein m=1.

5. A process according to claim 1 wherein A is S.

6. A process according to claim 1 wherein A is O.

7. A process according to claim 1 wherein said dithiocarboxylic ester is selected form the group consisting of benzyl dithiobenzoate, benzyl-4-methoxydithiobenzoate, benzyl-4-fluorodithiobenzoate, benzyl-4-nitrodithiobenzoate, benzyl-4-cyanodithiobenzoate, benzyl-4-trifluoromethyldithiobenzoate, diphenyldithiobenzoate, propyl dithiobenzoate, benzyl dithiopropionate, and benzyl-4-chlorodithiobenzoate.

8. A process for the preparation of a dithiocarboxylic ester compound, said process comprising:

(a) reacting a compound of formula $R^3(COAH)_m$ and a compound of structure II

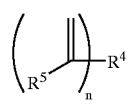

in the presence of a clay catalyst; and (b) treating products of the reaction with a thiating agent to produce a compound of structure III, a compound of structure IV, or a combination of compounds of structure III and structure IV;

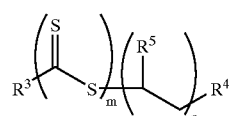

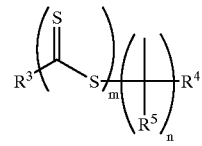

wherein $R^3$ is selected from the group consisting of alkyl, substituted alkyl, aryl, substituted aryl, heteroaryl, substituted heteroaryl;

$R^4$ is a n-valent radical selected from the group consisting of alkyl, substituted alkyl, aryl, substituted aryl, heteroaryl, substituted heteroaryl;

$R^5$ is H or lower alkyl;

A is S or O;

m and n are independently integers from 1–6, with the proviso that when m>1, n=1 and when n>1, m=1.

9. A process according to claim 8 wherein substitutents of said substituted alkyl, substituted aryl, substituted alkylaryl and substituted heteroaryl are independently chosen from alkyl, halogen, lower alkoxy, cyano, hydroxy and haloalkyl.

10. A process according to claim 8 wherein $R^3$ is selected from the group consisting of alkyl, aryl, and substituted aryl; and $R^4$ is selected from the group consisting of alkyl, aryl, and heteroaryl.

11. A process according to claim 8 wherein A is S.

12. A process according to claim 8 wherein A is O.

13. A process according to claim 8 wherein the compound of structure III is selected from the group consisting of vinyl compounds, olefins, acrylates, methacrylates, styrene and substituted styrenes.

14. A process according to claim 8 wherein $R^4$ is aryl.

15. A process according to claim 8 wherein $R^5$ is H or methyl.

16. A process according to claim 8 wherein the compound of structure II is an olefin.

17. A process according to claim 8 wherein the compound of structure II is styrene.

18. A process according to claim 8 wherein the compound of structure II is a substituted styrene.

19. A process according to claim 8 wherein the compound of structure II is a vinyl compound.

20. A process according to claim 8 wherein the compound of structure II is an acrylate.

21. A process according to claim 8 wherein the compound of structure II is a methacrylate.

22. A process according to claim 8 wherein m=1 and n=1.

23. A process according to claim 8 wherein the thiating agent is Lawesson's reagent.

24. A process according to claim 8 wherein said dithiocarboxylic ester is selected form the group consisting of compounds of structures 1–10:

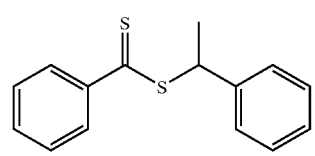

1

-continued
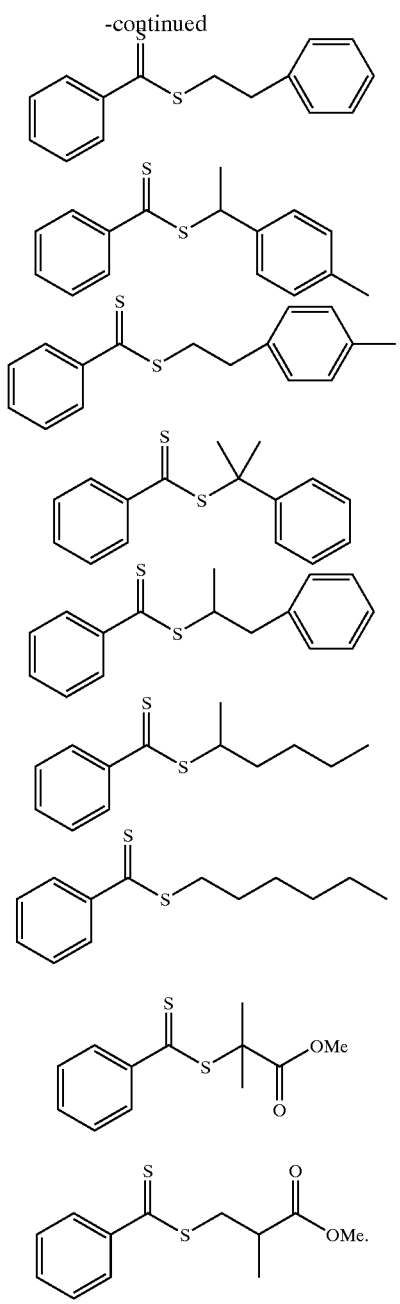
25. A dithiocarboxylic ester selected from the group consisting of:
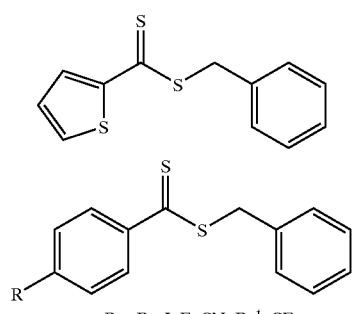
-continued
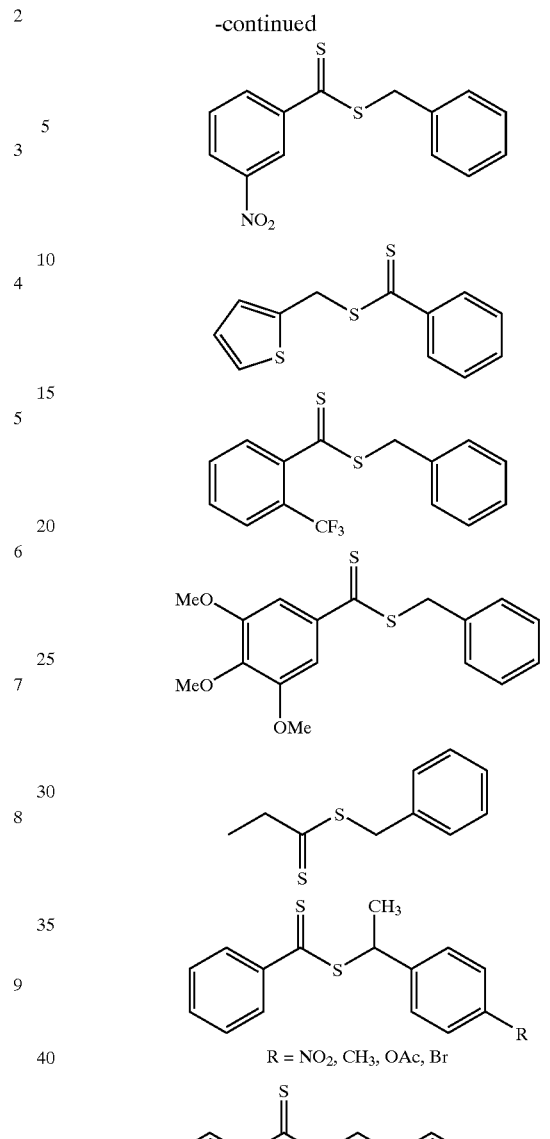
* * * * *